(12) United States Patent
Sansoucy

(10) Patent No.: US 10,039,899 B2
(45) Date of Patent: Aug. 7, 2018

(54) MULTIPLE LUMEN CATHETERS

(71) Applicant: Covidien LP, Mansfield, MA (US)

(72) Inventor: Michael Sansoucy, Wrentham, MA (US)

(73) Assignee: Covidien LP, Mansfield, MA (US)

( * ) Notice: Subject to any disclaimer, the term of this patent is extended or adjusted under 35 U.S.C. 154(b) by 882 days.

(21) Appl. No.: 14/039,642

(22) Filed: Sep. 27, 2013

(65) Prior Publication Data

US 2015/0094670 A1   Apr. 2, 2015

(51) Int. Cl.
*A61M 25/00* (2006.01)
*B29C 65/02* (2006.01)

(52) U.S. Cl.
CPC ...... *A61M 25/0043* (2013.01); *A61M 25/003* (2013.01); *A61M 25/0009* (2013.01); *B29C 65/02* (2013.01); *A61M 25/0023* (2013.01); *A61M 25/0069* (2013.01); *A61M 25/0071* (2013.01); *A61M 2025/0031* (2013.01); *A61M 2025/0081* (2013.01); *Y10T 29/49826* (2015.01)

(58) Field of Classification Search
CPC ...... A61M 2025/0031; A61M 25/0032; A61M 25/003; A61M 25/007; A61M 25/0068; A61M 25/0026
See application file for complete search history.

(56) References Cited

U.S. PATENT DOCUMENTS

| | | |
|---|---|---|
| 5,167,623 A | 12/1992 | Cianci et al. |
| 5,195,962 A * | 3/1993 | Martin ............... A61M 25/001 604/43 |
| 5,221,256 A | 6/1993 | Mahurkar |
| 5,224,938 A | 7/1993 | Fenton, Jr. |
| 5,395,316 A | 3/1995 | Martin |
| 7,776,005 B2 | 8/2010 | Haggstrom et al. |
| 8,062,247 B2 | 11/2011 | Abe et al. |
| 8,092,415 B2 | 1/2012 | Moehle et al. |
| 8,394,218 B2 | 3/2013 | Sansoucy |

(Continued)

FOREIGN PATENT DOCUMENTS

| | | |
|---|---|---|
| CN | 1878583 A | 12/2006 |
| CN | 102631240 A | 8/2012 |

(Continued)

OTHER PUBLICATIONS

Extended Search Report from counterpart European Patent Application No. 14181982.1, dated Mar. 9, 2015, 9 pp.

(Continued)

*Primary Examiner* — Bradley J Osinski

(74) *Attorney, Agent, or Firm* — Kenneth Collier; Jessica Kwak Rauckman

(57) ABSTRACT

A catheter includes an elongate body having a proximal portion and a distal portion, and a tip having a proximal portion coupled to a distal portion of the elongate body along a longitudinal axis of the elongate body. The elongate body and tip together define a first lumen and a second lumen. The elongate body further defines a third lumen extending distally to a body opening defined by the elongate body and in fluid communication with the third lumen. A cross-sectional area, orthogonal to the longitudinal axis, of at least one of the first and second lumens increases from a point proximal to the body opening to a point distal to the body opening.

17 Claims, 3 Drawing Sheets

(56) References Cited

U.S. PATENT DOCUMENTS

| | | | |
|---|---|---|---|
| 2004/0006318 A1 | 1/2004 | Periakaruppan et al. | |
| 2005/0113798 A1 | 5/2005 | Slater et al. | |
| 2006/0004325 A1* | 1/2006 | Hamatake | A61M 1/3653 604/43 |
| 2006/0009740 A1 | 1/2006 | Higgins et al. | |
| 2008/0154186 A1 | 6/2008 | Appling et al. | |
| 2008/0249501 A1 | 10/2008 | Yamasaki | |
| 2009/0126867 A1 | 5/2009 | Decant, Jr. et al. | |
| 2010/0081986 A1 | 4/2010 | Matson et al. | |
| 2011/0054415 A1* | 3/2011 | Onuma | A61M 25/0075 604/247 |
| 2011/0077577 A1 | 3/2011 | Sansoucy | |

FOREIGN PATENT DOCUMENTS

| | | | |
|---|---|---|---|
| EP | 2289590 A1 | 3/2011 | |
| WO | 0132240 A1 | 5/2001 | |

OTHER PUBLICATIONS

First Office Action and Search Report, and translation thereof, from counterpart Chinese Application No. 201410500276.6, dated Dec. 2, 2016, 14 pp.

Third Office Action and Search Report, and translation thereof, from counterpart Chinese Application No. 201410500276.6, dated Jan. 24, 2018, 15 pp.

Second Office Action and Search Report, and translation thereof, from counterpart Chinese Application No. 201410500276.6, dated Jul. 7, 2017, 15 pp.

\* cited by examiner

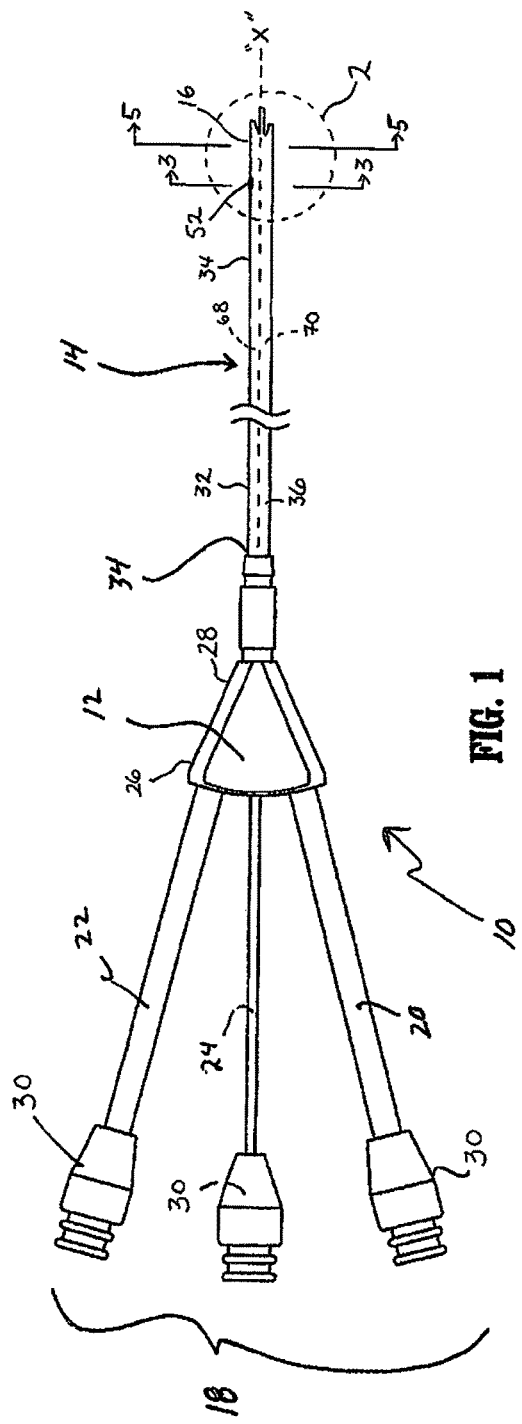
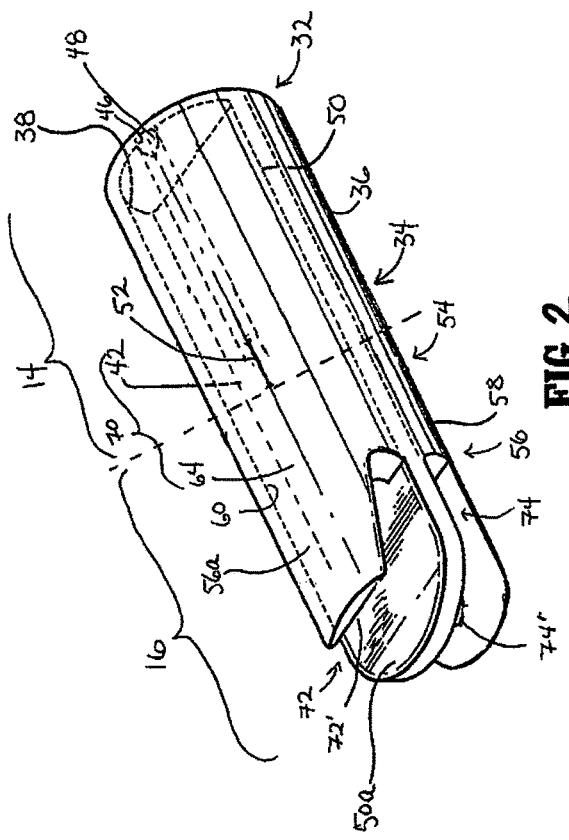

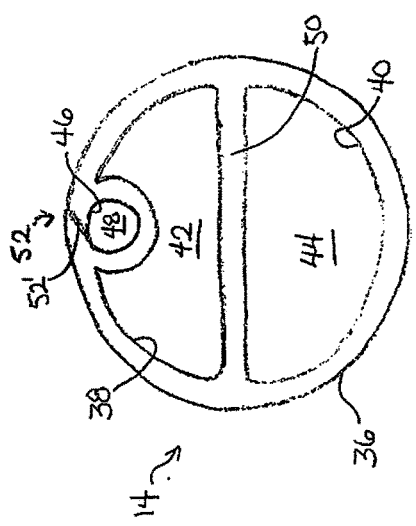
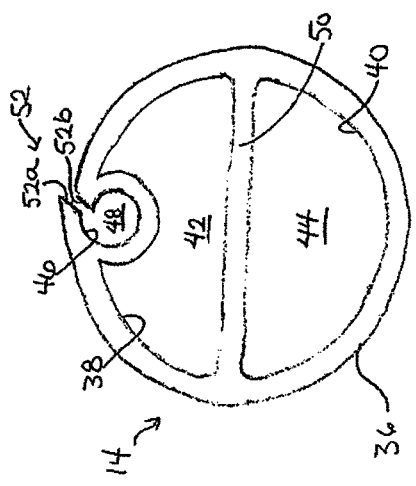
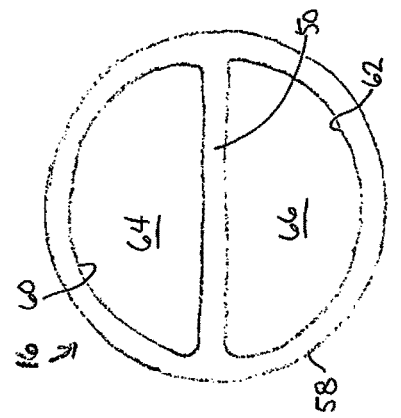
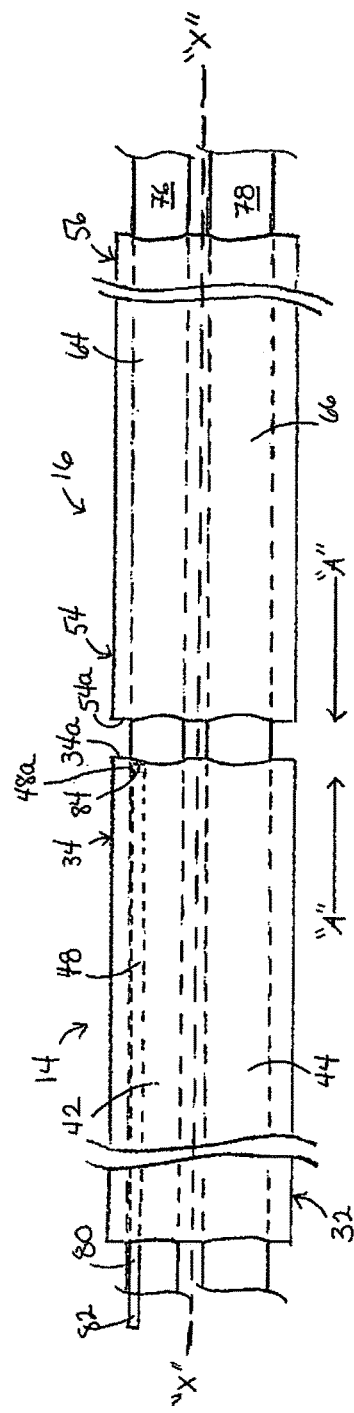

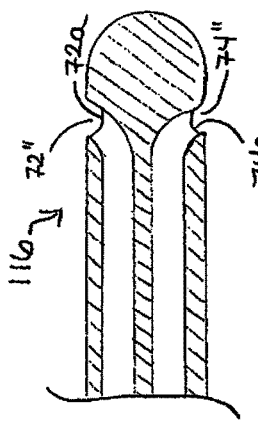
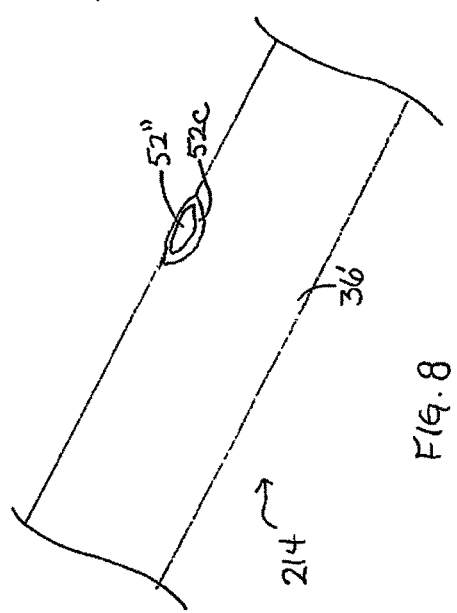
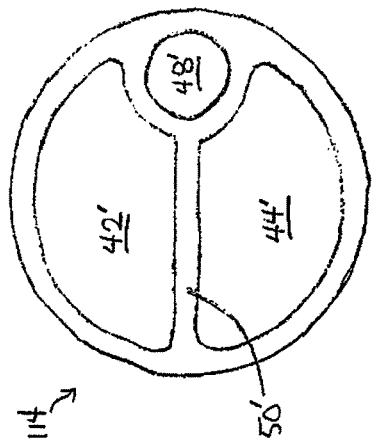
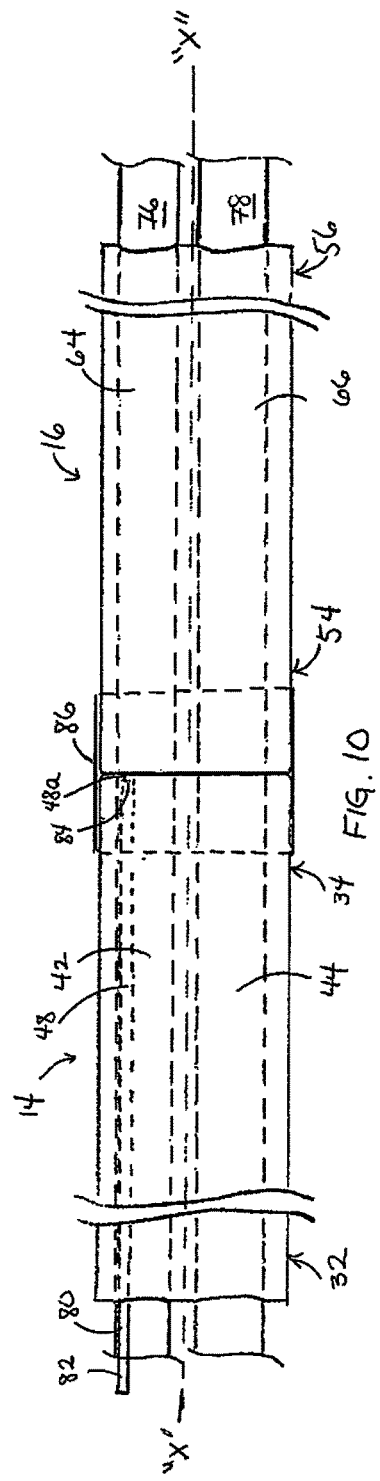

MULTIPLE LUMEN CATHETERS

TECHNICAL FIELD

The present disclosure generally relates to catheters, and more particularly, to multiple lumen catheters.

BACKGROUND

Catheters are flexible medical instruments that facilitate withdrawal and introduction of fluids from and to body cavities, ducts, and vessels. Catheters may have particular application, for example, in a hemodialysis procedure where blood is withdrawn from a blood vessel for treatment, and subsequently returned to the blood vessel for circulation. During some hemodialysis procedures, a multiple lumen catheter is inserted into a body and blood is withdrawn through an arterial lumen of the catheter. The removed blood is directed, via an extension tube, to a hemodialysis machine which dialyzes the blood to remove waste and toxins. The purified blood is then returned through a venous lumen of the catheter.

The efficiency and performance of a hemodialysis procedure may be reduced due to unbalanced flow between the arterial and venous lumens and/or low recirculation at the tip of the catheter, as well as occlusion due to thrombus formation at the tip openings.

SUMMARY

The present disclosure is directed to multiple lumen catheters having low recirculation during medical procedures (e.g., hemodialysis) while simultaneously allowing for the infusion of medication, blood sampling, and/or pressure measurement.

In one aspect of the present disclosure, a catheter includes an elongate body having a proximal portion and a distal portion and defining a longitudinal axis, and a tip having a proximal portion coupled to the distal portion of the elongate body along the longitudinal axis. The elongate body and the tip together define a first lumen and a second lumen. The elongate body further defines a third lumen extending distally to a body opening defined by the elongate body and in fluid communication with the third lumen. A cross-sectional area, orthogonal to the longitudinal axis, of at least one of the first and second lumens increases from a point proximal to the body opening to a point distal to the body opening.

In certain embodiments, the cross-sectional area of at least of the first and second lumens is larger in the tip than in the elongate body.

In some embodiments, the elongate body has a higher durometer than the tip.

In certain embodiments, the first and second lumens are symmetrical along the length of at least one of the elongate body and the tip.

In some embodiments, the body opening is a normally closed slit that is defined by a side wall of the elongate body. The slit can be movable from a closed position to an open position under the force of fluid moving through the third lumen.

In certain embodiments, the body opening is a normally open aperture through a side wall of the elongate body.

In some embodiments, the elongate body has a substantially uniform outer diameter along a length of the elongate body defining the first and second lumens. The tip can have a substantially uniform outer diameter equal to the substantially uniform outer diameter of the elongate body.

In certain embodiments, the third lumen terminates distally at the proximal portion of the tip.

In some embodiments, the distal portion of the tip defines first and second tip end distal openings in fluid communication with the respective first and second lumens. In some embodiments, the first and second tip end distal openings are coterminous with one another. In certain embodiments, the tip defines first and second tip side openings in fluid communication with the respective first and second lumens. For example, the first and second tip side openings can be diametrically opposed to one another.

In some embodiments, a septum is disposed in the elongate body and in the tip. The septum can define a portion of each of the first lumen and the second lumen. Additionally or alternatively, the septum defines at least a portion of the third lumen.

In certain embodiments, the first and second lumens are coterminous with one another. Additionally or alternatively, the first and second lumens can be substantially D-shaped along the elongate body and the tip.

In another aspect, a catheter includes an elongate body defining a first proximal lumen, a second proximal lumen, and a third proximal lumen, with each proximal lumen extending along a longitudinal axis defined by the elongate body, and a tip having a proximal end portion coupled to the elongate body along the longitudinal axis. The tip defines first and second distal lumens in fluid communication with respective first and second proximal lumens. The third proximal lumen distally terminates at the proximal end portion of the tip. The elongate body defines a body opening in fluid communication with the third lumen, and the tip defines coterminous first and second tip distal openings in fluid communication with the respective first and second distal lumens.

In some embodiments, the elongate body has a higher durometer than the tip.

In certain embodiments, the elongate body has a substantially uniform outer diameter along a length of the elongate body defining the first and second proximal lumens. Additionally or alternatively, the tip may have a substantially uniform outer diameter equal to the substantially uniform outer diameter of the elongate body.

In some embodiments, the tip defines first and second side openings in fluid communication with the respective first and second lumens. The first and second side openings can be diametrically opposed to one another.

In yet another aspect, a method of manufacturing a catheter includes approximating a distal end portion of an elongate body relative to a proximal end portion of a tip along a longitudinal axis defined by the elongate body, positioning first and second mandrels in respective first and second lumens defined by the approximation of the elongate body and the tip, introducing beading into a third lumen defined by the elongate body, and bonding the distal end portion of the elongate body with the proximal end portion of the tip. A first end of the beading extends out of a proximal end of the elongate body and a second end of the beading is disposed proximate to the distal end portion of the elongate body. A distal end portion of the third lumen is sealed between the elongate body and the tip.

In some embodiments, bonding includes heating the elongate body and the tip and axially compressing the elongate body and the tip relative to one another. In certain embodiments, bonding includes placing a shrink tube over the elongate body and the tip and applying thermal energy to the shrink tube.

Embodiments can include one or more of the following advantages.

In some embodiments, the catheter defines first, second, and third lumens, with portions of the first and second lumens distal to the third lumen having the same general shape and cross-sectional area, and symmetrical tip openings to facilitate uniform and balanced blood flow through the tip. Additionally or alternatively, the symmetrical arrangement of the tip openings creates outlet and inlet blood flow patterns which reduce the likelihood of recirculation during operation of the catheter.

In some embodiments, the catheter defines a body opening proximal to a tip of the catheter. As compared to triple-lumen catheters having three lumens terminating at a tip, the definition of a body opening proximal to the tip can reduce transitions in shape in the vicinity of the tip and, for example, reduce the likelihood of thrombus formation. Additionally or alternatively, the formation of the body opening of the third lumen as a normally closed slit can reduce the likelihood of thrombus formation in the vicinity of the body opening by providing, for example, a unidirectional valve that opens only upon fluid infusion through the third lumen. In the normally closed position, the slit maintains a smooth outer surface of the catheter and laminar blood flow over the closed body opening with very little shear, which can reduce the likelihood of thrombus formation at the body opening.

In certain embodiments, catheters are formed through coupling (e.g., welding) extruded components to one another. As compared to triple-lumen catheters in which components must be molded to achieve a configuration having first, second, and third lumens, the coupling of extruded components to one another to form a triple-lumen catheter is a simple and repeatable process that can result in less time and/or wasted material during the manufacturing process.

Other aspects, features, and advantages will be apparent from the description, drawings, and the claims.

BRIEF DESCRIPTION OF THE DRAWINGS

FIG. 1 is a side elevation view of a catheter including a tube assembly, a catheter hub, an elongate body, and a tip.

FIG. 2 is an enlarged, perspective view of a portion of the elongate body and the tip of the catheter of FIG. 1, shown along the area of detail 2 identified in FIG. 1.

FIG. 3 is a cross-sectional view of the elongate body of the catheter of FIG. 1, taken along lines 3-3 of FIG. 1, showing a body opening of the elongate body in a closed position.

FIG. 4 is a cross-sectional view of the elongate body of the catheter of FIG. 1, similar to the view of FIG. 3, showing a body opening of the elongate body in an open position.

FIG. 5 is a cross-sectional view of the tip of the catheter of FIG. 1, taken along line 5-5 of FIG. 1;

FIG. 6 is side view of the elongate body and the tip of the catheter of FIG. 1, with mandrels and beading shown in phantom during manufacture of the catheter of FIG. 1.

FIG. 7 is a cross-sectional view of an elongate body of a catheter.

FIG. 8 is a partial perspective view of an elongate body of a catheter defining a body opening.

FIG. 9 is a side cross-sectional view of a tip of a catheter.

FIG. 10 is a side view of the elongate body and the tip of the catheter of FIG. 1, with mandrels and beading shown in phantom during a step of manufacture.

DETAILED DESCRIPTION

The exemplary embodiments of the catheter and methods of manufacture are disclosed and discussed in terms of medical catheters for the administration and/or withdrawal of fluids relative to the body of a subject, and more particularly, in terms of a hemodialysis catheter. However, it should be appreciated that the present disclosure may be used in a range of catheter applications including surgical, diagnostic, and related treatments of diseases or body ailments of a subject. It should be further appreciated that the principles relating to the disclosed catheter include use with various catheter-related procedures, such as, for example, hemodialysis, cardiac, abdominal, urinary, intestinal, and in chronic and/or acute applications. Moreover, the catheter can be used for administration or withdrawal of fluids such as, for example, medication, saline, bodily fluids, blood, and/or urine.

In the following discussion, the term "proximal" or "trailing" refers to the portion of a structure closer to a clinician, while the term "distal" or "leading" refers to the portion of the structure further from the clinician. As used herein, the term "subject" refers to a human subject or other animal. The term "clinician" refers to a doctor, nurse, or other care provider and may include support personnel.

Referring now to FIG. 1, a catheter 10 includes a catheter hub 12, an elongate body 14 extending from the catheter hub 12, and a tip 16 at a distal end region of the elongate body 14. The catheter 10 may include an extension tube assembly 18 having first, second, and third extension tubes 20, 22, 24.

In use, the elongate body 14 is advanced along a guidewire and/or passed through a sheath positioned within a subject's vasculature such that the tip 16 is adjacent or within the treatment site. The extension tubes 20, 22 are coupled to an extracorporeal treatment device (e.g., a hemodialysis machine), and the treatment device is activated. Blood is drawn from the vasculature through the tip 16 and directed through a lumen of the elongate body 14 to the treatment device. The blood is treated by the treatment device and returned through another lumen of the elongate body 14 and delivered from the tip 16 into the vasculature.

The catheter hub 12 is dimensioned for manual engagement by the clinician. The catheter hub 12 includes a proximal housing section 26 adjacent the extension tubes 20, 22, 24 and a distal housing section 28 adjacent the elongate body 14. The proximal housing section 26 is attachable to the first, second, and third extension tubes 20, 22, 24 and the distal housing section 28 is attachable to the elongate body 14 in secured relation therewith. The catheter hub 12 can be secured to the extension tubes 20, 22, 24 and/or the elongate body 14 through one or more of the following: an interference or frictional fit, bonding, welding, and/or use of cements or adhesives. The catheter hub 12 may further include a pair of opposed wings extending outwardly from the catheter hub 12 to facilitate attachment of the catheter hub 12 to a subject by suturing.

The first and second extension tubes 20, 22 connect to either the inflow or outflow ports of a treatment device to transfer blood between the subject and the treatment device. The third extension tube 24 may be fluidly coupled to an infusion source (e.g., saline, medicaments, and/or a contrast media) via a luer adapter 30. Each extension tube 20, 22, 24 may include a respective luer adapter 30 at its free end for connection to the inflow and outflow ports of the treatment device and the source of irrigation, aspiration, or infusion. Additionally or alternatively, a clamp may be mounted about each extension tube 20, 22, 24 to control fluid flow.

Referring now to FIGS. 1-4, the elongate body 14 includes a proximal portion 32 and a distal portion 34, and defines a central longitudinal axis "x." The elongate body 14 may be substantially circular in cross-section along the entire length of the elongate body 14. In some embodiments, the elongate body 14 has a substantially uniform outer diameter along the entire length of the elongate body 14. In certain embodiments, the elongate body 14 has a substantially uniform outer diameter along portions of the length of the elongate body 14 (e.g., along the proximal portion 32 and/or along the distal portion 34).

The elongate body 14 is a tri-lumen catheter including a side wall 36 forming at least a portion of first, second, and third inner surfaces 38, 40, 46, respectively. The first inner surface 38 defines a first proximal lumen 42, the second inner surface 40 defines a second proximal lumen 44, and the third inner surface 46 defines a third lumen 48. Opposing portions of the first and second inner surfaces 38, 40 define at least a portion of a septum 50 between the first and second proximal lumens 42, 44 to separate the first and second proximal lumens 42, 44 from fluid communication with one another. Each of the first and proximal lumens 42, 44 extends along (e.g., parallel to) the longitudinal axis "x" of the elongate body 14. The first and second proximal lumens 42, 44 are in fluid communication with the first and second extension tubes 20, 22, respectively, and the third lumen 48 is in fluid communication with the third extension tube 24.

Each of the first and second proximal lumens 42, 44 is substantially D-shaped in cross-section. As compared to other configurations, the substantially D-shaped cross-section of the first and second proximal lumens 42, 44 can facilitate formation of the first and second proximal lumens 42, 44 through an extrusion process. Additionally or alternatively, as compared to other configurations, the substantially D-shaped cross-section of the first and second proximal lumens 42, 44 can facilitate the passage of a large volume of fluid through the first and second proximal lumens 42, 44 while the overall shape of the elongate body 14 is maintained within a circular profile. Additionally or alternatively, as compared to co-axial configurations of lumens, the ratio of internal surface area to open area of the side-by-side orientation of the first and second proximal lumens 42, 44 reduces the amount of force required to move fluid through the first and second proximal lumens 42, 44. In some embodiments, the first and second proximal lumens 42, 44 are symmetrical relative to the septum 50. For example, the cross-sectional area, defined along a plane orthogonal to the longitudinal axis "x," of each of the first and second proximal lumens 42, 44 may be constant along the entire length of the elongate body 14. The second proximal lumens 44 has a larger cross-sectional area than the first proximal lumen 42, with the third inner surface 46 defining the third lumen 48 disposed entirely within the first proximal lumen 42.

The third lumen 48 defines a circular cross-sectional area along a plane perpendicular to the longitudinal axis "x" and is constant along the length of the elongate body 14. However, it should be appreciated that other cross-sectional areas, such as oval, elliptical, or polygonal shape, are also with the scope of this disclosure. In some embodiments, the circular cross-sectional area of the third lumen 48 increases along at least a portion of the length of the elongate body 14 in a direction from the catheter hub 12 toward the tip 16.

The elongate body 14 is at least partially flexible and can be at least partially formed of silicone or a biocompatible polyurethane. For example, the elongate body can be fabricated from polyurethane having a durometer Shore hardness between about 70 A to about 80 D (e.g., between about 75 A to about 55 D) or, more specifically, about 85 A. Additionally or alternatively, the side wall 36 of the elongate body 14 may include reinforcing material and/or additives. The elongate body 14 can be straight or have a pre-curved configuration in the absence of an external stressor (e.g., to conform to a body cavity or vessel in which the elongate body 14 is to be positioned).

The third lumen 48 is adjacent a portion of the first inner surface 38. The cross-sectional area of the third lumen 48 in a plane perpendicular to the longitudinal axis "x" is less than the cross-sectional area of the first proximal lumen 42 in the same plane. For example, the cross-sectional area of the third lumen 48 can be less than about 20 percent of the area of the first proximal lumen 42 such that a sufficient volume of fluid can be infused through the third lumen 48 while maximizing the amount of blood that can be moved through the first proximal lumen 42.

The third inner surface 46 extends along the longitudinal axis "x" of the elongate body 14 and terminates distally at a body opening 52 defined in the side wall 36 of the elongate body 14. The body opening 52 is disposed along the elongate body 14 at a point proximal to the tip 16. For example, the body opening 52 can be defined adjacent to a proximal portion 54 of the tip 16.

The body opening 52 is a normally closed slit 52' in fluid communication with the third lumen 48 and, in some embodiments, allows for fluid infusion when the static pressure in the third lumen 48 is greater than the static pressure adjacent the outside of the slit 52'. This positive pressure differential between the third lumen 48 and the treatment site may be established by, for example, attaching a syringe, infusion pump, or other fluid source to the luer adapter 30 of the third extension tube 24 and using the syringe, infusion pump, or other fluid source to create the positive pressure differential sufficient to open the body opening 52. The slit 52' may include one or more beveled edges 52a, 52b that open in response to infused fluids. The beveled edges 52a, 52b can, for example, reduce the likelihood that the slit 52' would open inwardly, into the third lumen 48, under a negative pressure condition in which the static pressure at the treatment site is greater than the static pressure in the third lumen 48.

With reference now to FIGS. 1, 2, and 5, the tip 16 includes the proximal portion 54 and a distal portion 56. The proximal portion 54 of the tip is coupled to the distal portion 34 of the elongate body 14 such that the tip 16 extends from the distal portion 34 of the elongate body 14 in a direction parallel to the central longitudinal axis "x." The proximal portion 54 of the tip 16 has a cross-sectional area, in a plane perpendicular to the longitudinal axis "x," substantially equal (e.g., differing by less than 2%) to a cross-sectional area of the distal portion 34 of the elongate body 14 in the same plane. Such substantially equal cross-sectional areas can reduce disruption in fluid flow at the point of connection between the elongate body 14 and the tip 16. The tip 16 can be connected to the elongate body 14 by welding, molding, shrink-wrapping, adhesives, and/or other suitable techniques.

The tip 16 may have a substantially constant cross-section (e.g., a circular cross-section), in a plane perpendicular to the longitudinal axis "x," along at least a majority of the tip 16. Additionally or alternatively, the cross-sectional area of the tip 16 in the plane may taper down in a direction extending from the proximal portion 54 to the distal portion 56. Such a tapered configuration can facilitate, for example, positioning the tip 16 at the treatment site.

The tip 16 includes a side wall 58 forming first and second inner surfaces 60, 62. The first inner surface 60 defines a first distal lumen 64, and the second inner surface 62 defines a second distal lumen 66. The first distal lumen 64 is aligned, and in fluid communication with the first proximal lumen 42 to define a first lumen 68, and the second distal lumen 66 is aligned, and in fluid communication, with the second proximal lumen 44 to define a second lumen 70. Accordingly, the first and second distal lumens 64, 66 may define the same cross-sectional shape (e.g., D-shaped) as the first and second proximal lumens 42, 44. The first and second inner surfaces 60, 62 define at least a portion of the septum 50 such that the septum 50 is disposed in both the elongate body 14 and the tip 16 and defines a portion of each of the first and second lumens 68, 70.

The first and second distal lumens 64, 66 are symmetrically arranged relative to the septum 50 and relative to each other. Because the third lumen 48 of the elongate body 14 terminates proximate to the tip 16, at least one of the first and second lumens 68, 70 may increase in cross-sectional area from a point proximal to the body opening 52 to a point distal to the body opening 52. For example, at least one of the first and second distal lumens 64, 66 may have a larger cross-sectional area, in a plane perpendicular to the longitudinal axis "x," than the respective first and second proximal lumen 42, 44 at a point proximal to the body opening 52. Additionally or alternatively, at least one of the first and second distal lumens 64, 66 may have the same cross-sectional area, along at least a portion of the tip 16, as the respective first and second proximal lumen 42, 44 with which it is aligned.

In some embodiments, the tip 16 includes a material having a lower durometer than the durometer of the material of the elongate body 14. Such a lower durometer tip 16 can reduce the likelihood of trauma to the vasculature as the catheter 10 is advanced through the vasculature to the treatment site while the higher durometer of the material of the elongate body 14 can reduce the amount of force required to advance the catheter through the vasculature.

The first and second distal lumens 64, 66 terminate at respective first and second tip openings 72, 74. The first and second tip openings 72, 74 are distal tip openings 72', 74' defined at a distal end portion 56a of the tip 16 and are in fluid communication with respective first and second lumens 68, 70. The first and second distal tip openings 72', 74' may be coterminous with each other to facilitate, for example, reversing flow through the catheter 10 while maintaining low recirculation of flow through the distal tip openings 72', 74' as compared to catheter configurations including staggered tip openings. In certain embodiments, the septum 50 includes a septum extension 50a that extends distally beyond the first and second distal lumens 64, 66. The septum extension 50a can additionally or alternatively facilitate reversing flow through the catheter 10 while maintaining low circulation of flow through the distal tip openings 72', 74'.

Referring now to FIG. 6, a method of manufacturing the catheter 10 includes approximating a distal end portion 34a of the distal portion 34 of the elongate body 14 relative to a proximal end portion 54a of the proximal portion 54 of the tip 16 along the longitudinal axis "x" in the direction of arrows "A." A first mandrel 76 is positioned in the first proximal lumen 42 and in the first distal lumen 64, and a second mandrel 78 is positioned in the second proximal lumen 44 and in the second distal lumen 66. Beading 80 is introduced into the third lumen 48 such that a first end 82 of the beading 80 extends proximally out of the proximal portion 32 of the elongate body 14 and a second end 84 of the beading 80 is disposed proximate to the distal end 34a of the distal portion 34 of the elongate body 14. In some embodiments, the distal portion 34 of the elongate body 14 and the proximal portion 54 of the tip 16 are approximated subsequent to positioning the first and second mandrels 76, 78 such that the elongate body 14 and tip 16 are skewered together by the first and second mandrels 76, 78. The distal end 34a of the elongate body 14 is bonded to the proximal end 54a of the tip 16 such that a distal end 48a of the third lumen 48 is sealed between the elongate body 14 and the tip 16. In certain embodiments, bonding the elongate body 14 to the tip 16 includes butt welding the elongate body 14 to the tip 16. Additionally or alternatively, bonding the elongate body 14 to the tip 16 can include heating the elongate body 14 and the tip 16 and axially compressing the elongate body 14 and the tip 16 relative to one another in the direction of arrows "A." As another non-exclusive example, the elongate body 14 and the tip 16 may be placed in a die prior to heating, and the elongate body 14 and the tip 16 may be axially compressed to one another.

The body opening 52 of the third lumen 48 may be formed by cutting, punching, and/or ablating the slit 52' (FIG. 3) through the side wall 36 of the proximal portion 32 of the elongate body 14 at a position lateral to the sealed distal end 48a of the third lumen 48. The first and second mandrels 76, 78 and/or the beading 80 may be removed prior or subsequent to forming the body opening 52.

While certain embodiments have been described, other embodiments are possible.

For example, while catheters have been described as having substantially D-shaped proximal lumens, other configurations are additionally or alternatively possible. For example, the first and second proximal lumens can be kidney-shaped, oblong-shaped, C-shaped, circular, pie-shaped in a plane perpendicular to a longitudinal axis of the catheter.

As another example, while catheters have been described as having a third lumen disposed within a first proximal lumen such that the first proximal lumen and a second proximal lumen have different cross-sectional areas, other configurations are additionally or alternatively possible. For example, referring now to FIG. 7, an elongate body 114 defines first and second proximal lumens 42', 44' separated by a septum 50'. One diametral end of the septum 50' is bifurcated to define at least a portion of a third lumen 48'. The first and second proximal lumens 42', 44' are symmetrical and can have the same cross-sectional area along the entire length of the elongate body 114. Such symmetry of the first and second proximal lumens 42', 44' can facilitate the reversibility of the catheter 10 in use with reduced likelihood of a degradation in performance of the catheter 10 in a first orientation relative to a second, reversed orientation.

As yet example, while catheters have been described as having a body opening including a slit, other configurations are additionally or alternatively possible. For example, referring now to FIG. 8, an elongate body 214 includes a side wall 36' defining a body opening that is a normally open aperture 52" that can be in fluid communication with a third lumen. The aperture 52" may have contoured edges 52c formed, for example, by cross cutting or laser cutting the exterior surface of the side wall 36'. Such contoured edges 52c can, for example, facilitate the withdrawal of a blood sample through the aperture 52" by reducing the likelihood of thrombosis at the aperture 52".

As still another example, while catheters have been described as having distal tip openings, other configurations are additionally or alternatively possible. For example, referring to FIG. 9, a tip 116 may define side tip openings 72", 74" proximal to a distal end of the tip 116. The side tip openings 72", 74" are diametrically opposed relative to one another and can be in fluid communication with respective first and second lumens (e.g., first and second lumens similar to the first and second lumens 68, 70 in FIG. 1). In some embodiments, the first and second side tip openings 72", 74" have a substantially elongate, ovular configuration. In certain embodiments, at least a portion of each of the first and second side tip openings 72", 74" faces a distal end of the tip 116. Additionally or alternatively, the first and second side tip openings 72", 74" may have contoured or curved edges 72a, 74a formed, for example, by laser cutting or during extrusion or molding of the tip 116, and/or otherwise smoothed to minimize flow disruption and thrombus formation.

As another example, while methods of securing an elongate body to a tip to form a catheter have been described, other methods are additionally or alternatively possible. For example, referring to FIG. 10, bonding may be achieved by placing a shrink tube 86 over the elongate body 14 and the tip 16 and applying thermal energy to the shrink tube 86.

A number of embodiments have been described. Nevertheless, it will be understood that various modifications may be made without departing from the spirit and scope of the disclosure. Accordingly, other embodiments are within the scope of the following claims.

What is claimed is:

1. A catheter comprising:
an elongate body having a proximal portion and a distal portion, the proximal portion and the distal portion defining a longitudinal axis; and
a tip having a proximal portion coupled to the distal portion of the elongate body along the longitudinal axis, the elongate body and the tip together defining a first lumen and a second lumen, the elongate body further defining a third lumen extending distally to a body opening defined by the elongate body and in fluid communication with the third lumen, and a cross-sectional area, orthogonal to the longitudinal axis, of at least one of the first and second lumens increasing from a point proximal to the body opening to a point distal to the body opening, wherein the body opening is a normally closed slit defined by a side wall of the elongate body, and the slit is movable from a closed position to an open position under the force of fluid moving through the third lumen, wherein the tip defines first and second tip side openings, the first tip side opening in fluid communication with the first lumen and the second tip side opening in fluid communication with the second lumen, and wherein the first and second tip side openings are diametrically opposed to one another.

2. The catheter of claim 1, wherein the cross-sectional area of at least one of the first and second lumens is larger in the tip than in the elongate body.

3. The catheter of claim 1, wherein the elongate body has a higher durometer than the tip.

4. The catheter of claim 1, wherein the first and second lumens are symmetrical along the length of at least one of the elongate body or the tip.

5. The catheter of claim 1, wherein the elongate body has a substantially uniform outer diameter along a length of the elongate body defining the first and second lumens.

6. The catheter of claim 5, wherein the tip has a substantially uniform outer diameter equal to the substantially uniform outer diameter of the elongate body.

7. The catheter of claim 1, wherein the third lumen terminates distally at the proximal portion of the tip.

8. The catheter of claim 1, wherein a distal end portion of the tip defines first and second tip end distal openings in fluid communication with the respective first and second lumens, the first and second tip end distal openings coterminous with one another.

9. The catheter of claim 1, further comprising a septum disposed in the elongate body and the tip, the septum defining a portion of each of the first lumen and the second lumen, and the septum defining at least a portion of the third lumen.

10. The catheter of claim 1, wherein the first and second lumens are coterminous with one another.

11. The catheter of claim 1, wherein the first and second lumens are substantially D-shaped along the elongate body and the tip.

12. A catheter comprising:
an elongate body defining a first proximal lumen, a second proximal lumen, and a third proximal lumen, each proximal lumen extending along a longitudinal axis defined by the elongate body; and
a tip having a proximal end portion coupled to the elongate body along the longitudinal axis, the tip defining first and second distal lumens in fluid communication with respective first and second proximal lumens, the third proximal lumen distally terminating at the proximal end portion of the tip, the elongate body defining a body opening in fluid communication with the third lumen, and the tip defining coterminous first and second tip distal openings in fluid communication with the respective first and second distal lumens, wherein the body opening is a normally closed slit defined by a side wall of the elongate body, and the slit is movable from a closed position to an open position under the force of fluid moving through the third lumen, and, wherein the tip defines first and second side apertures, the first side aperture in fluid communication with the first distal lumen and the second side aperture in fluid communication with the second distal lumen, and wherein the first and second side apertures are diametrically opposed to one another.

13. The catheter of claim 12, wherein the elongate body has a higher durometer than the tip.

14. The catheter of claim 12, wherein the elongate body has a substantially uniform outer diameter along a length of the elongate body defining the first and second proximal lumens, and the tip has a substantially uniform outer diameter equal to the substantially uniform outer diameter of the elongate body.

15. A method of manufacturing a catheter, the method comprising:
approximating a distal end portion of an elongate body relative to a proximal end portion of a tip along a longitudinal axis defined by the elongate body;
positioning first and second mandrels in respective first and second lumens defined by the approximation of the elongate body and the tip;
introducing beading into a third lumen defined by the elongate body such that a first end of the beading extends out of a proximal end of the elongate body and a second end of the beading is disposed proximate to the distal end portion of the elongate body;

bonding the distal end portion of the elongate body with the proximal end portion of the tip such that a distal end portion of the third lumen is sealed between the elongate body and the tip;

forming a normally closed slit in a side wall of the elongate body and in fluid communication with the third lumen, wherein the slit is movable from a closed position to an open position under the force of fluid moving through the third lumen; and forming first and second side openings in the tip, wherein the first tip side opening is in fluid communication with the first lumen and the second tip side opening is in fluid communication with the second lumen, and wherein the first and second tip side openings are diametrically opposed to one another.

16. The method of claim 15, wherein bonding the elongate body and the tip includes heating the elongate body and the tip and axially compressing the elongate body and the tip relative to one another.

17. The method of claim 15, wherein bonding the proximal and distal members includes placing a shrink tube over the elongate body and the tip and applying thermal energy to the shrink tube.

* * * * *